(12) United States Patent
Oberhauser

(10) Patent No.: US 6,190,550 B1
(45) Date of Patent: Feb. 20, 2001

(54) MONITORING HIGH PERFORMANCE LIQUID CHROMATOGRAPHY

(75) Inventor: Charles J. Oberhauser, Belmont, MA (US)

(73) Assignee: Cohesive Technologies, Inc., Frankline, MA (US)

(*) Notice: Under 35 U.S.C. 154(b), the term of this patent shall be extended for 0 days.

(21) Appl. No.: 09/408,714

(22) Filed: Sep. 30, 1999

(51) Int. Cl.$^7$ .................................................. B01D 15/08
(52) U.S. Cl. ........................................ 210/198.2; 210/656
(58) Field of Search .................................... 210/635, 656, 210/659, 198.2

(56) References Cited

U.S. PATENT DOCUMENTS

| | | | | |
|---|---|---|---|---|
| 5,795,469 | * | 8/1998 | Quinn .................................. | 210/198.2 |
| 5,919,368 | * | 7/1999 | Quinn .................................. | 210/198.2 |
| 5,968,367 | * | 10/1999 | Quinn .................................. | 210/198.2 |

OTHER PUBLICATIONS

Snyder, Introduction to Modern Liquid Chromatography, John Wiley & Son, Inc., New York, 1979, p. 161–162.*

* cited by examiner

*Primary Examiner*—Ernest G. Therkorn
(74) *Attorney, Agent, or Firm*—Schiller & Associates

(57) ABSTRACT

A method of monitoring performance of liquid chromatography apparatus comprising an elongated chromatography column and having a conduit coupled to the column inlet for introducing a flow of liquid into said column preferably at very high pressure. Variations in a selected electromagnetic property, such as the electrical conductivity, of the liquid flow are measured, preferably in the conduit. Apparatus is configured so that respective volumes of sample liquid and eluant may be introduced into the conduit sequentially or substantially simultaneously with substantially no band-spreading when flowing through the conduit into the column. A pair of electrically conductive electrodes, coupled to metering means, are positioned at two spaced-apart locations within the conduit and are electrically insulated from each other and from the ends of the conduit.

14 Claims, 3 Drawing Sheets

MONITORING HIGH PERFORMANCE LIQUID CHROMATOGRAPHY

This invention relates generally to chromatography and more particularly to apparatus for and methods of monitoring improved high performance liquid chromatographic systems.

BACKGROUND OF THE INVENTION

High performance liquid chromatography is effected generally by percolating a number of component solute molecules in a flowing stream of a liquid through a packed bed of particles, known as the stationary phase, which efficiently separates the various types of molecules from one another.

Such separations, particularly in the preparative area, have significant limitations typically occasioned by the batch nature of the current processes. Typically, a chromatographic column is first equilibrated by flowing a liquid through the column. The latter is then charged or loaded with a fluid mixture containing the solute or solutes sought to be separated, and one or more eluant liquids or an eluant gradient are run sequentially through the column to release bound solute selectively. The eluted solutes, usually in relatively minute quantities, are thus temporally separated at the output of the column and the process is repeated cyclically. It is highly desirable to verify the intended changes in solution composition that actually arrive at the inlet of the chromatographic column in the intended manner. It may also be desirable to monitor the time-varying output of the column which provides an indication of band-spreading due to mixing of adjacent volumes of different solvents in the input conduits and the column itself, and malfunctions in the eluant gradient generating devices or other malfunctions which may cause undesirable behavior of the system. In chromatographic systems typical of the prior art, the electrical input used to control the gradient generator also generate the display of the gradient profile, and does not provide any measurement of the actual fluid output of the gradient generator. Consequently, malfunctions (even as common and trivial as running out of solvent) that create gradient conditions other than those intended, will only be noted when the chromatographic separation fails to yield the desired result, i.e. when it is too late to resolve.

Conventional or standard detectors are designed generally to be installed downstream from the chromatographic column where the pressure level is the lowest in the system and where the desired solute has been diluted as a result of the separation process. The material or solute, as it is detected at the outlet of the column, is generally in a much larger volume of solvent than when it is introduced at the input to the column. The greater volume of the peak to be detected at the column outlet means that band-spreading in the detector can be greater without any major effect on the overall separation, and because the more dilute conditions require a more sensitive detector, usually a larger detector cell is provided which tends to produce even more band-spreading. Since the pressure requirements imposed on detectors placed at the column output are very modest, the detector designs are slanted toward high sensitivity and it is doubtful that currently used detectors are capable of sustaining the pressure levels commonly present at the inlet to HPLC columns. Even if such detectors were strengthened to meet such pressure demands, because they tend to introduce excessive band-spreading, they would not adequately serve as detectors for the column inlet.

The foregoing considerations are, a fortiori, important in the context of certain novel methods and apparatus for performing HPLC at the very high inlet pressures required to insure that flow through the chromatographic column occurs at a reduced velocities of greater than about 5,000, a highly efficient chromatography system described more fully in U.S. Pat. Nos. 5,772,874, 5,795,469 and 5,919,368, the same being incorporated in their entirety herein by reference.

OBJECTS OF THE INVENTION

A principal object of the present invention is to provide improved monitoring for chromatographic apparatus and processes effecting high capacity, high resolution separation of solutes. Other objects of the present invention are to provide such chromatographic apparatus and processes that respond very quickly to changes in composition, that do not introduce significant band-spreading, and are particularly useful in the separation of high molecular weight products such as biologicals and the like. Yet other objects of the present invention are to provide such apparatus and processes as will enable monitoring of fluid flow through preparative chromatographic apparatus employing large pressure levels at the column input; and particularly to provide such monitoring of fluid flow in chromatographic apparatus in which reduced velocities through the column are effected at levels preferably greater than about 5000.

SUMMARY OF THE INVENTION

To these ends the present invention is directed to novel methods and apparatus for monitoring liquid chromatography apparatus, and for monitoring liquid chromatography apparatus employing relatively high inlet pressures typically characteristic of equipment employing the principles set forth in the aforesaid U.S. Pat. Nos. 5,772,874, 5,795,469 and 5,919,368. Accordingly, the invention comprises a method of monitoring performance of liquid chromatography apparatus comprising an elongated chromatography column having conduit means coupled to the column for effecting a flow of liquid through the column, in which method, changes in selected electromagnetic properties of liquid flowing through the conduit are measured. To this end, in one embodiment, the invention comprises chromatography apparatus including the usual chromatographic column together with means for controlling the injection of sample liquid and eluant liquid into and/or out of the column through the conduit means or conduit. In a preferred embodiment, the internal dimensions and configuration of the conduit and the inlet to the column are selected so that the liquid volumes of eluant and sample experience substantially no band-spreading when flowing through the device. For example, the cross-section dimensions and geometry of the conduit are selected to provide fluid flow paths at both the inlet and outlet of the column that have substantially identical dimensions and geometry. Means are coupled to the conduit for measuring selected electromagnetic properties of liquid flowing therethrough, for example, the electrical conductivity of the liquids in the conduit. Other electromagnetic properties of the liquid in the conduit that may be measured alone or in combination are the electrical capacitance, magnetic susceptibility, electrical resistance and the like. It should be understood that the liquid in the conduit, with respect to its electromagnetic properties, refers to not only the liquid per se but that liquid in combination with any solute or suspended material therein. In a preferred embodiment, the means for measuring the selected electromagnetic properties preferably comprises detector means for detecting the selected property and means for measuring the property so detected. To this end, in one embodiment, the detector means includes at least a pair of surfaces responsive to the electromagnetic properties and disposed at spaced-apart locations with respect to the conduit, the responsive surfaces being formed of electrically conductive material, with the adjacent conduit surfaces being formed of substantially electrically non-conductive or insulating material. In yet another embodiment, the means for controlling the injection of sample and eluant fluids into the column preferably serves to introduce respective volumes of the liquids into an input conduit substantially simultaneously at spatially separated locations so that the liquids travel through the column at a common group velocity as closely bunched liquid plugs.

The invention is intended in one particular embodiment to be applicable to chromatography apparatus of the type described in the aforesaid U.S. Pat. Nos. 5,772,874, 5,795,469 and 5,919,368. In such apparatus it is particularly desirable to flow fluid plugs of sample and eluant through the column at an average reduced velocity of at least about 5000, inasmuch as such reduced velocity is believed to be sufficient to induce turbulent flow of the fluids within at least a major portion of the interstitial volume between the particles. The term "plug" as used herein in connection with injected volumes is to be understood to mean a mass or volume of fluid that is injected into a flowstream in a chromatographic column so as to form a discrete, essentially isomorphic mass extending substantially completely across the column and preferably having approximately flat or planar front and rear surfaces extending perpendicular to the axis of elongation of the column.

Because to achieve such a reduced velocity generally requires unusually large input pressure at the column inlet, where the detector means for detecting the selected electromagnetic properties of fluid is located at or adjacent the inlet of the column, in such instance the detector means is desirably rugged enough to withstand such pressure. In one embodiment as hereinafter described in detail, the simple provision of a pair of surfaces disposed in spaced-apart relation within the conduit and responsive to the electromagnetic properties easily meets this criterion.

The foregoing and other objects of the present invention will in part be obvious and will in part appear hereinafter. The invention accordingly comprises the apparatus possessing the construction and arrangement of parts exemplified in the following detailed disclosure, and the method comprising the several steps and the relation and order of one or more of such steps with respect to the others, the scope of the application of which will be indicated in the claims.

For a fuller understanding of the nature and objects of the present invention, reference should be had to the following detailed description taken in connection with the drawings wherein line numerals denote like parts.

DETAILED DESCRIPTION

Figure 1:
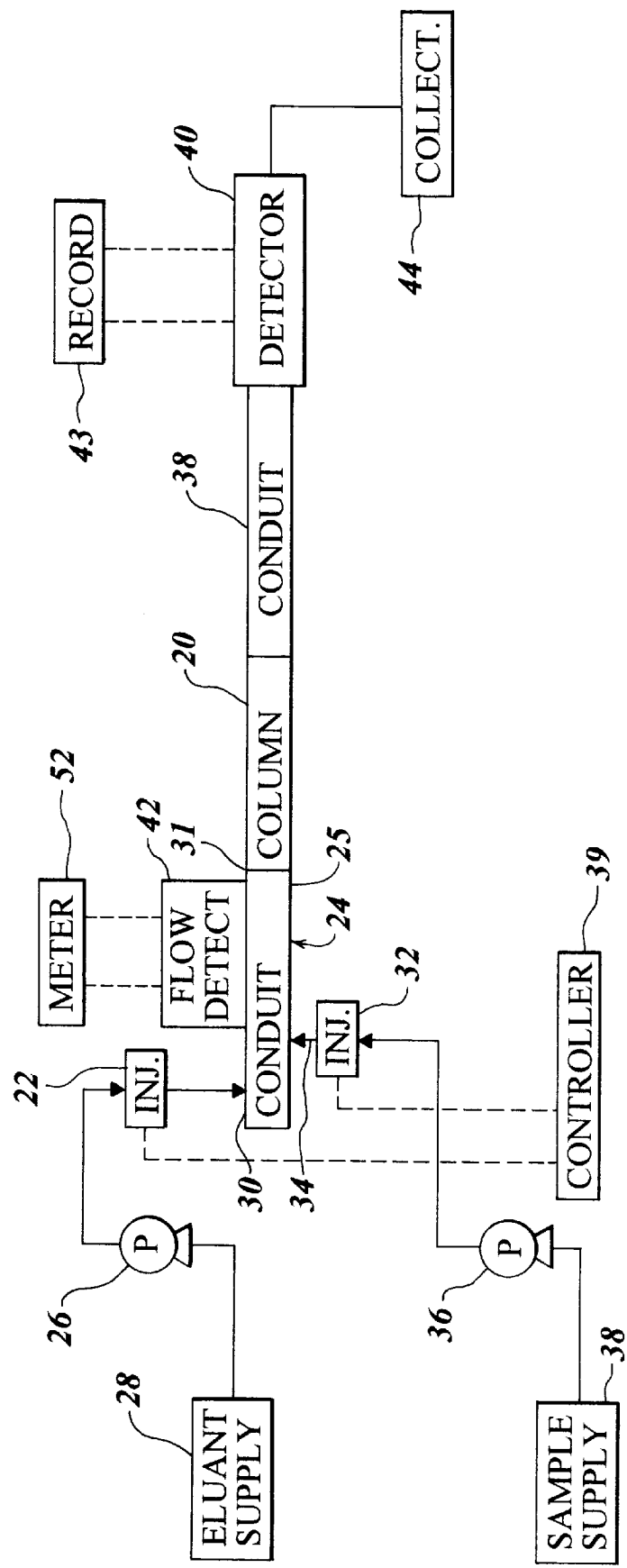
FIG. 1 is a schematic diagram of apparatus embodying the principles of the present invention in which lines carrying liquid are depicted as unbroken and lines carrying electrical signals are depicted as broken.
Figure 2:
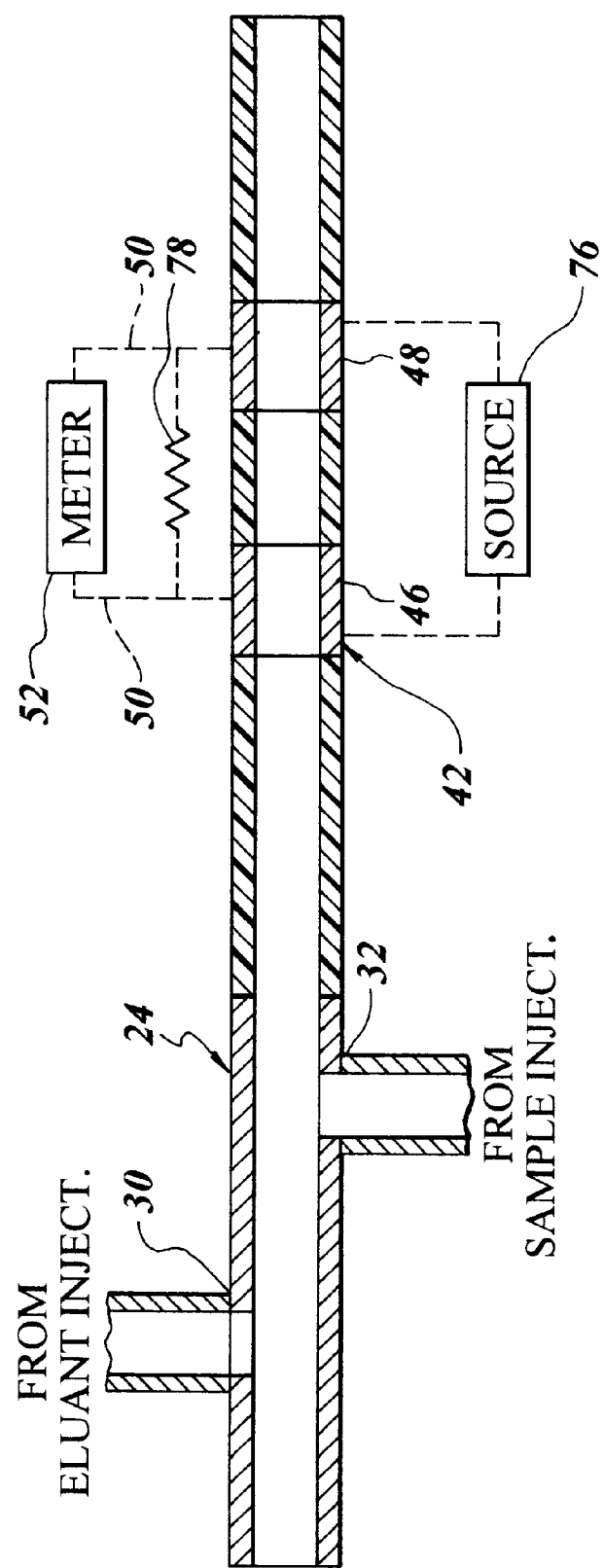
FIG. 2 is a schematic cross-section of a conduit of the present invention incorporating means for measuring selected electromagnetic properties of fluid in the conduit.

One aspect of the present invention, as shown schematically in FIGS. 1 and 2, is embodied in chromatography apparatus comprising a chromatographic column 20 formed for example, as a packed multiplicity of rigid, solid particles (not shown) which in a preferred embodiment typically have substantially uniform mean diameters of not less than about 30 $\mu$m as described in the aforesaid U.S. Pat. Nos. 5,772,874, 5,795,469 and 5,919,368. In view of the preferred high input pressure to the column, the particles in the column when used in the present invention are preferably formed from materials that are incompressible, which term is to be understood to mean that the time rate of changes of the densities and volumes of the particles under pressures of at least about $5 \times 10^3$ psi, (including outlet column frit retainer) remains substantially zero, and the particles therefore will substantially resist deformation even at such high pressure. The surfaces of the particles in column 20 are chromatographically active either per se as is well known in the art, or by treatment, as by coating, with any of the many known chromatographically active, stationary phase layers, also as well known in the art.

The chromatography apparatus used in present invention preferably includes means such as a first loop injector 22 for injecting a volume of eluant fluid into conduit means 24, a portion of which, conduit 25, is coupled directly to the input to column 20. Eluant fluid is provided to injector 22, for example by an auxiliary means, such as first pump means 26 for pumping eluant fluid from an appropriate source such as eluant supply reservoir 28. The output of first pump means 26 is coupled to first location 30 in conduit 25. The distal or outlet end of conduit 25 is connected at junction 31 to the inlet or proximal end of column 20. The pressure provided by first pump means 26 and first injector 22 is, for example, at a level high enough so that the eluant fluid provided flows through at least a major portion of the interstitial volume in column 20, preferably at an average reduced velocity, v, substantially above about 5000.

The apparatus used in the present invention further includes means, such as second loop injector 32 for injecting plugs of fluid sample mixture at another location 34 into conduit 25. Typically, where the present invention is being employed for preparative purposes, the plug of sample mixture provided by second injector 32 will be as large as practicable to load column 20 fully. The sample mixture contains solute or solutes of interest, and is pumped into second injector 32 by second auxiliary pump 36 from another appropriate reservoir or sample storage supply 38. Injectors useful in the present invention are commercially sold as, for example, Model 3725 and Model 3725-038 injectors available from Rheodyne Incorporated of Cotati, California, and similar injectors provided by several other manufacturers.

In the embodiment shown in FIGS. 1 and 2, the outputs of injectors 22 and 32 are connected to input conduit 25 at different respective locations 30 and 34 spaced apart from one so that injections at the two locations can be made either sequentially or simultaneously if desired. The internal dimensions and configuration of conduit 25 and of the inlet or proximal end of column 20 at junction 31 are matched such that the fluid volumes injected into the conduit means experience substantially no band-spreading when flowing through the latter through junction 31 into column 20. Operation of each injector is preferably under the control of known types of controller 39 and can be manually controlled or automatically controlled to inject respective plugs of sample mixture and eluant fluid into the proximal end of column 20, preferably at average reduced velocities above about 5000. In one embodiment, controller 40 may include a known gradient generator so that the controller not only determines the timing of injection by injectors 22 and 32, but also controls the eluant composition. The injectors may be operated to inject the respective liquid plugs substantially simultaneously or in a timed sequence. Where the injection coil in injector 32 is sized, for example, to deliver a 1 mL plug, the corresponding coil in injector 22 may be sized to provide a plug of, e.g., 0.5 mL of liquid. It will be apparent that the spacing and location of the sample and eluant injectors relative to the input conduit may be other than that shown in the drawings.

It will be appreciated that pumps 26 and 36 may be any desired type of known pump and are not to be limited to mechanical pumps, but may be any known system for imposing pressure on the respective fluid to cause the latter to flow at the desired flow rate.

The plug of sample mixture flowing through column 20 serves to load the latter as solute molecules become bound to chromatographically active surfaces in the column. The distal or output end of column 20 is connected, in the embodiment shown, to one end of conduit 38, the latter being another portion of conduit means 24, so that the solute molecules eluted from the column by the eluant fluid are detected, typically optically by solute detector 40, of a type and in a manner well known in the prior art, disposed at the distal end of conduit 38. The values determined by detector 40 are measured, displayed and/or recorded on means 43. The various bands of solute and eluant fluid are collected at the distal end of column 20 in collection means 44. For superior results, the eluant flow through column 20 is preferably provided at a velocity corresponding to a reduced velocity of above about 5000, so that band spreading of solute eluted by the eluant fluid from the column in the present invention is an inverse function of the Reynolds number for the eluant fluid and the magnitude of the diffusion coefficient of the solute in the eluant fluid.

While the apparatus of the present invention has been described in terms of a chromatographic column of packed particles, as described in the aforementioned U.S. Pat. Nos. 5,772,874, 5,795,469 and 5,919,368, the columns useful in the present invention can also be in the alternative form of a capillary tube defining a hollow, elongated channel of substantially uniform internal diameter, the channel being provided with a chromatographically active interior surface. The tube is formed such that turbulent flow will be induced in fluid pumped through the interior at a velocity sufficient to create substantial eddies in the fluid.

One or more flow detectors means 42 for detecting selected electromagnetic properties or parameters in the fluid flowing through conduit means 24, forms part of or is or are mounted within or adjacent conduit means 24 downstream from locations 30 and 32. Accordingly, it will be appreciated that flow detector means 42 can be located anywhere within the flow path of the liquid being subjected to chromatographic separation, e.g. at or adjacent either conduit 25 or conduit 38 respectively coupled to the proximal and distal ends of column 20. Alternatively, multiple such flow detector means can be provided, each located in, at or adjacent a respective conduit if one wishes to monitor the flow at several points along the flow path such as at both the input and output ends of column 20.

Figure 3:
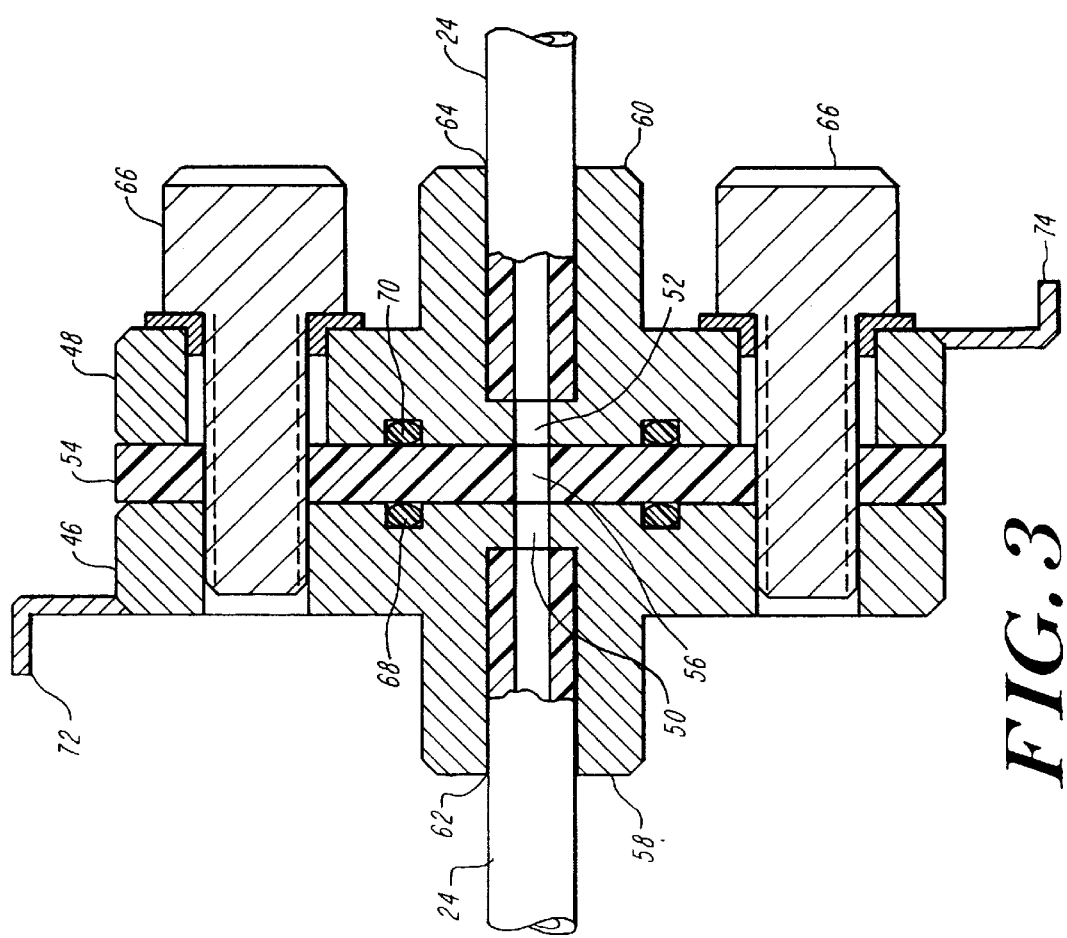
FIG. 3 is a cross-sectional view through of one embodiment of a detector means forming part of the present invention.

FIG. 3 is illustrative of a detailed embodiment of detector means 42, and comprises a pair of surfaces such as electrodes 46 and 48, typically formed as apertured disks made of strong, electrically conductive material, typically a metal such as stainless steel or the like. Electrodes 46 and 48, in the embodiments of FIGS. 2 and 3, are longitudinally spaced apart from one another, coaxially about the flow path provided for fluid to flow through conduit means 24. Electrodes 46 and 48 each have central apertures 50 and 52 respectively, dimensioned to match the internal dimensions and geometry of conduit means 24. Disk or spacer 54 is provided between electrodes 46 and 48 so as to electrically isolate the latter from one another, spacer 54 being formed of an strong, electrically insulating or dielectric material such as, but not limited to, synthetic polymers such as PEEK (a polyethetherketone commercially available from Upchurch Scientific, Oak Harbor, Wash.), ceramics, rubber and the like. Spacer 54 includes a central aperture 56 disposed coaxially with and dimensioned and shaped to match the internal dimensions of conduit means 24. The materials from which spacer 54 and electrodes 46 and 48 are formed, are preferably chemically non-reactive with any of the sample mixture and eluant fluid chosen to flow through conduit means 24. The materials chosen for the conduit and electrodes should have sufficient material bulk and strength to withstand high input pressures, typically up to several thousand psi provided to achieve the desired average reduced flow rate of above about 5000 in column 20.

Both electrodes 46 and 48 are provided centrally with respective hub portions 58 and 60 having identical central apertures 62 and 64 extending through the respective electrodes normal to the plane of the disk, apertures 62 and 64 having internal dimensions enlarged to match the outside diameter of conduit means 24 and respectively portions of which are disposed coaxially with apertures 50 and 52. Thus, when those portions of conduit means 24 are respectively emplaced in apertures 62 and 64, the external dimension of the conduit means, being matched to the internal dimensions of apertures 62 and 64 are tightly fitted therein. Because the internal cross-section and geometry of conduit means 24 is matched to the dimensions and geometry of central aperture sections 50 and 52 of electrodes 46 and 48 and aperture 56 in spacer 54, a uniform flow path through detector means 42 is provided. As shown in FIG. 3, electrodes 46 and 48 and spacer 63 are all held together by cap screws 66. Preferably, O-rings 68 and 70 are disposed about apertures 50 and 52 between the surfaces at which electrodes 46 and 48 mate with spacer 54. Cap screws 66, if made of electrically conductive material, are electrically insulated from the electrodes by interposed insulating bushings, or can be made from very strong, electrically insulating material, per se, such as Delrin®, a known acetal resin, or the like.

The parameters detected by electrodes 46 and 48 are any desired electromagnetic properties, or changes in such properties, of fluid in conduit means 24 that extends the stream of solution through column 20. Measurement can be made of electromagnetic properties such as, but not limited to, electrical conductivity or conductance, electrical resistivity or resistance, dielectric constants, capacitance, magnetic permeability and the like. Accordingly, electrodes 46 and 48 are connected by electrically conductive leads 72 and 74 to a measuring or metering device such as any of several known types of meter means 52 (such as, but not limited to ammeters, ohmnmeters, voltmeters, and the like ) to measure, display and/or record the values of the electromagnetic properties detected by the electrodes. In a preferred embodiment, meter means 52 is a "virtual instrument" or measuring and data acquisition system comprising a digital computer operated by a software program named LabVIEW available commercially from National Instruments Corporation, Austin, Tex. Where, for example, a property to be measured is simply electrical conductivity, it will be appreciated that an electrical power source 76 can be provided simply and typically as a 6 volt DC source or battery, connected through a high resistance, such as a 10 KΩ resistor 78, across electrodes 46 and 48 by appropriate leads (not shown), to provide an output voltage to meter means 52. It should be appreciated that the electromagnetic parameters of fluid flowing in conduit 24 between electrodes 46 and 48 are not necessarily the same as parameters of electrically conductive solids and accordingly the fact that the fluids are typically electrolytes may have to be taken into consideration. Solutions typically obey Ohm's law as do metallic conductors, except under certain exceptional conditions. Generally, measurement of conductivity with direct current tends to liberate gases at the electrodes, increasing the resistance, and also sets up a counter or polarization emf that opposes the passage of current. Thus as well known, measurements can typically also be made with alternating current using a Wheatstone bridge, avoiding substantial gasification.

Where the conductivity of a dilute solution is being measured, then conductance theory asserts that the limiting equivalent conductance of an electrolyte is due to the sum of the independent migration of anions and cations. For such electrolytes Ohm's law does not accurately apply inasmuch as the equivalent conductance of an electrolyte increases with the applied voltage, reaching a theoretical maximum at some high voltage. This effect is specially pronounced in weak organic acids, the weaker the acid, the stronger the effect, and the magnitude of the effect is a function of the concentration of the solute, and the dielectric constant, viscosity and temperature of the solvent. Also, the presence of a number of different ions of a given polarity in the solution will complicate the interpretation of measurement of resistivity or conductivity. Accordingly, it will be appreciated that meter means 52 should be calibrated as taught in any definitive electrochemistry textbook to compensate for any variations due to such measurements being made in solution rather than in solid conductors.

Figure 4:
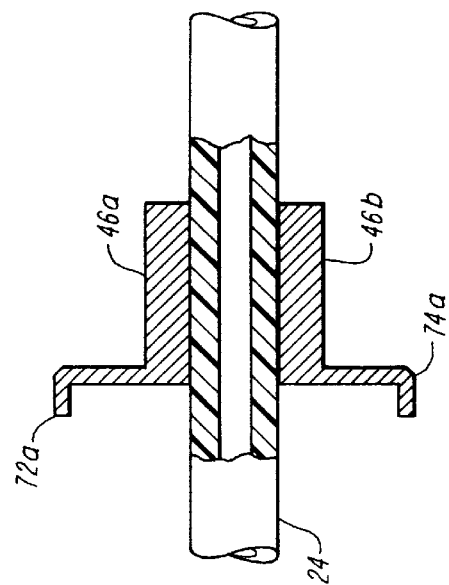
FIG. 4 is a cross-sectional view through of yet another embodiment of a detector means forming part of the present invention.

In yet another embodiment of the detector of the present invention as shown in FIG. 4, differing substantially only in the geometry of the detector, electrodes 46a and 48a are formed as semi-cylindrical elements disposed opposite one another transversely to the flow path through conduit means 24, rather than opposite one another longitudinally as in the embodiment of FIG. 3. Leads 72a and 74a are provided for connecting this embodiment to meter means 52.

Since certain changes may be made in the above apparatus and process without departing from the scope of the invention herein involved, it is intended that all matter contained in the above description or shown in the accompanying drawing shall be interpreted in an illustrative and not in a limiting sense.

What is claimed is:

1. In liquid chromotography apparatus including a substantially uniform, elongated chromatography column having conduit means coupled to at least one end of said column for extending the flow path of fluid through said column, and means for flowing said fluid through said conduit means, the improvement comprising;

means for measuring at least one selected electromagnetic property of said fluid in the flow of said fluid substantially within said conduit means, the internal cross-section dimensions of said conduit means and said one end of said column being so matched that said fluid experiences substantially no pressure change when flowing through between said conduit means and said one end of said column.

2. In liquid chromatography apparatus as set forth in claim 1 wherein said means for measuring is sensitive to changes in said electromagnetic property.

3. In liquid chromatography apparatus as set forth in claim 1 wherein said means for measuring comprises detector means for detecting said electromagnetic property in said fluid flowing through said conduit means, and metering means for computing, displaying and/or recording the values of said electromagnetic property detected by said detector means.

4. In liquid chromatography apparatus as set forth in claim 3 wherein at least a portion of said conduit means is connected to the inlet end of said column.

5. In liquid chromatography apparatus as set forth in claim 3 wherein at least a portion of said conduit means is connected to the outlet end of said column.

6. In liquid chromatography apparatus as set forth in claim 3 having at least one or more portions of said conduit means connected to either or both of the inlet end and/or the outlet end of said column.

7. In liquid chromatography apparatus as set forth in claim 6 wherein said detector means includes at least a pair of electrodes responsive to said electromagnetic property and disposed at two spaced-apart locations in at least one of said portions of said conduit means.

8. In liquid chromatography apparatus as set forth in claim 7 wherein said electrodes are longitudinally spaced apart from one another along an axis defined by the extended flow path through said at lest one of said portions of said conduit means.

9. In liquid chromatography apparatus as set forth in claim 7 wherein said electrodes are spaced apart from one another and disposed transversely to an axis defined by the extended flow path through said at least one of said portions of said conduit means.

10. In liquid chromatography apparatus as set forth in claim 7 wherein said electromagnetic property is the electrical conductivity of said fluid, and said electrodes comprise electrically conductive material.

11. In liquid chromatography apparatus as set forth in claim 7 wherein said detector means defines at least part of said flow path.

12. In liquid chromatopraphy apparatus as set forth in claim 7 including electrically insulating material disposed so as to electrically isolate said electrodes from each other and from said conduit means and said column.

13. In liquid chromatography apparatus as set forth in claim 12 wherein said electrically insulating material and said electrodes are formed of material mechanically strong enough to withstand the highest pressure of said liquid at the inlet to said column.

14. In liquid chromatography apparatus as set forth in claim 1 including a plurality of different sources of said fluid and wherein the means for flowing said fluid from through said conduit means is operable for flowing said fluid from said sources through said column sequentially or substantially simultaneously.

* * * * *